US010004883B2

(12) United States Patent
Anderson (10) Patent No.: US 10,004,883 B2
(45) Date of Patent: Jun. 26, 2018

(54) CONTEXTUAL ACTIVATION OF PHARMACEUTICALS THROUGH WEARABLE DEVICES

(71) Applicant: Intel Corporation, Santa Clara, CA (US)

(72) Inventor: Glen J. Anderson, Beaverton, OR (US)

(73) Assignee: Intel Corporation, Santa Clara, CA (US)

( * ) Notice: Subject to any disclaimer, the term of this patent is extended or adjusted under 35 U.S.C. 154(b) by 261 days.

(21) Appl. No.: 14/497,051

(22) Filed: Sep. 25, 2014

(65) Prior Publication Data

US 2016/0089524 A1 Mar. 31, 2016

(51) Int. Cl.
*G08C 17/02* (2006.01)
*A61M 31/00* (2006.01)
*A61M 5/172* (2006.01)
*A61M 5/142* (2006.01)

(52) U.S. Cl.
CPC ........... *A61M 31/002* (2013.01); *G08C 17/02* (2013.01); *A61M 5/14276* (2013.01); *A61M 5/1723* (2013.01); *A61M 2205/33* (2013.01); *A61M 2205/3303* (2013.01); *A61M 2205/3306* (2013.01); *A61M 2205/3317* (2013.01); *A61M 2205/3515* (2013.01); *A61M 2205/52* (2013.01); *A61M 2205/609* (2013.01); *A61M 2205/6009* (2013.01); *A61M 2205/6063* (2013.01); *A61M 2230/63* (2013.01)

(58) Field of Classification Search
None
See application file for complete search history.

(56) References Cited

U.S. PATENT DOCUMENTS

| 9,149,234 B2 * | 10/2015 | Kamath | A61B 5/7475 |
| 9,204,806 B2 * | 12/2015 | Stivoric | A61B 5/0008 |
| 2004/0158350 A1 | 8/2004 | Ostergaard et al. | |
| 2005/0043772 A1 | 2/2005 | Stahmann et al. | |
| 2005/0175665 A1 * | 8/2005 | Hunter | A61K 45/06 424/423 |
| 2006/0089856 A1 | 4/2006 | Kadhiresan et al. | |
| 2010/0185055 A1 * | 7/2010 | Robertson | A61B 5/0031 600/117 |
| 2011/0137114 A1 | 6/2011 | Schwartz et al. | |

(Continued)

FOREIGN PATENT DOCUMENTS

| WO | WO-2008112578 A1 | 9/2008 |
| WO | WO-2013033033 A1 | 3/2013 |
| WO | WO-2016048758 A1 | 3/2016 |

OTHER PUBLICATIONS

"International Application Serial No. PCT/US2015/050461, International Search Report dated Jan. 11, 2016", 8 pgs.

(Continued)

*Primary Examiner* — Uyen Le
(74) *Attorney, Agent, or Firm* — Schwegman Lundberg & Woessner, P.A.

(57) ABSTRACT

In some examples, a wearable device may emit signals to automatically release or activate drugs that are already in a user in response to a particular context of the user. For example, if the user begins vigorous exercise, the system may activate a pain medication that was already previously ingested by the user to alleviate anticipated joint pain.

25 Claims, 5 Drawing Sheets

(56) References Cited

U.S. PATENT DOCUMENTS

| | | | |
|---|---|---|---|
| 2011/0257491 A1* | 10/2011 | Robertson | A61B 5/0031 600/302 |
| 2011/0288379 A1 | 11/2011 | Wu | |
| 2012/0041778 A1* | 2/2012 | Kraft | B65D 51/2828 705/2 |
| 2012/0226093 A1* | 9/2012 | Creighton | H01F 7/0273 600/12 |
| 2014/0052464 A1* | 2/2014 | Ray | G06F 19/3418 705/2 |
| 2014/0214874 A1 | 7/2014 | Stivoric et al. | |
| 2014/0234938 A1* | 8/2014 | Langer | A61N 5/062 435/173.1 |
| 2014/0371816 A1* | 12/2014 | Matos | A61N 1/3727 607/59 |
| 2016/0004298 A1* | 1/2016 | Mazed | G06F 19/70 345/633 |
| 2017/0326033 A1* | 11/2017 | Kraft | A61J 7/0084 |

OTHER PUBLICATIONS

"International Application Serial No. PCT/US2015/050461, Written Opinion dated Jan. 11, 2016", 10 pgs.

Deok Kong, Seong, et al., "Magnetic field activated lipid-polymer hybrid nanoparticles for stimuli-responsive drug release", Acta Biomaterialia, 9(3), (Mar. 2013), 5447-5452.

Marcus, Jennifer, "Researchers develop magnetic molecular machines to deliver drugs to unhealthy cells", UCLA Newsroom (Science + Technology), [Online]. Retrieved from the Internet: <URL: http://newsroom.ucla.edu/releases/new-material-developed-for-use-165011>, (Aug. 9, 2010), 3 pgs.

"European Application Serial No. 15843991.9, Extended European Search Report dated Apr. 30, 2018", 7 pgs.

\* cited by examiner

CONTEXTUAL ACTIVATION OF PHARMACEUTICALS THROUGH WEARABLE DEVICES

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2014 Intel, Inc., All Rights Reserved.

TECHNICAL FIELD

Embodiments pertain to pharmaceuticals. Some embodiments relate to external activation of pharmaceuticals that are in the body. Further embodiments relate to the contextual activation of those pharmaceuticals.

BACKGROUND

Pharmaceuticals may be used for many purposes. Example usages include pain relief, treatment of a medical condition, treatment of an addiction, and other purposes. These pharmaceuticals may also have a variety of side effects. Examples side effects include liver damage and drowsiness. Conditional release pharmaceuticals in the bloodstream may alleviate some of these side effects. For example, time-released pharmaceuticals have been used extensively. Also, implanted pain-relief devices may administer drugs when a patient presses a button in response to pain. More recently, digital technologies have been employed to target the release of the pharmaceutical into the blood stream. For example, radio frequency (RF) fields have been used to activate anti-cancer drugs only in the area of the body that the drug is needed. The drug is contained in lipid-polymer hybrid nanoparticles that react to the magnetic field generated by the radio frequency signals.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

While these conditional release mechanisms alleviate side effects by targeting the release of the pharmaceutical in the blood stream, these mechanisms require user interaction. For example, when a user must take a time-released pill, it may take time for the drug's full effects to be realized. In the mean-time, the individual may experience discomfort or other problems. In the case of some anti-cancer drugs that use a radio frequency release mechanism, a health-care provider is needed to operate the radio frequency fields.

Disclosed in some examples are methods, machine readable mediums, and systems for automatic activation of pharmaceutical agents using wearable devices in response to detecting one or more contexts of the user, which indicate the need for pharmaceuticals. In some examples, a wearable device may emit signals to automatically release or activate drugs that are already in a user in response to a particular context of the user. For example, if the user begins vigorous exercise, the system may activate a pain medication that was already previously ingested by the user to alleviate anticipated joint pain.

A context of the user may indicate a current or predicted future state of the user. Contexts may include physical states such as running, walking, sleeping, or sitting. Contexts may include locations, such as restaurants, bars, health-care provider locations, and the like. Contexts may include more specific situations such as attending a particular meeting, going to the dentist's office, driving, and the like. Contexts may also include biometric states such as blood glucose levels, pain, heart function, and the like. The system may determine and in some cases anticipate situations in which the drug will be needed in order to ensure that the pharmaceutical has sufficient time to create the therapeutic effect to combat undesirable stress on the user caused by the situation. For example, the system may determine that the user is going to a dentist's office and the system may active an anti-anxiety medication prior to arriving such that the user is relaxed upon arrival. The system may utilize information about how much time it takes for a pharmaceutical to achieve a therapeutic effect as well as information on the user's schedule to time the activation to achieve a full therapeutic effect at the start of the dentist appointment.

The system may include a wearable device that includes a contextual engine which uses a variety of inputs to determine a context of a user that may trigger the generation of an activation field that activates the drug. Inputs may include sensor inputs—such as an accelerometer, impact sensors, geolocation sensor, heart monitors, pulse monitors, glucose monitors, blood oxygen sensors, brain wave sensors, and the like. Other inputs may include the user's calendar, email analysis, date and time information, point of interest information to provide context to a user's location, and the like. Further inputs may include a configuration of the contextual engine which may be set by a doctor, pharmacist, or other qualified individual. The inputs may be from sensors or data on the wearable device, or external to the wearable device.

Example usages include a pain medication sealed in nanoparticles already in the bloodstream which may be activated by a wearable device shortly before a scheduled physical therapy session. If the session is cancelled before the physical therapy, the drug may not be activated. The wearable device may be a wristband, watch, headband, waistband, chest strap, glasses, e-textile, or other device which may generate a magnetic field to release the pain medication.

Another example usage may be the administration of Antabuse. Antabuse is a drug that makes people feel sick when they drink alcohol. It is useful in treating alcoholism, but it does have undesirable side effects, thus limiting the amount in the user's system is desirable. Antabuse may be sealed in nanoparticles already in the user's bloodstream. When the user is in a restaurant that serves alcohol (as determined by sensors such as GPS), the wearable device activates the Antabuse nanoparticles in the bloodstream.

In other examples, alcoholic beverages may be labeled with an RFID sticker. The wearable device may scan for the unique code returned by the RFID sticker that indicates that alcohol is nearby. The wearable device could activate the Antabuse in response to detecting alcohol nearby. In other examples, the wearable device could have an alcohol sensor which may detect the odor of alcohol in the air or on the user's breath or in their blood. The wearable may activate the Antabuse in response to detecting the alcohol.

As another example, a sensor may be embedded in a leg brace that monitors for certain physical activity. After a threshold physical activity is met, an anti-inflammatory drug is activated by an RF radio on the leg brace to activate drug particles in a painful area under the leg brace.

In another example, an activation of an anti-anxiety drug may be activated before a user has an appointment with a person who causes anxiety in the user (e.g., a dentist).

Figure 1:
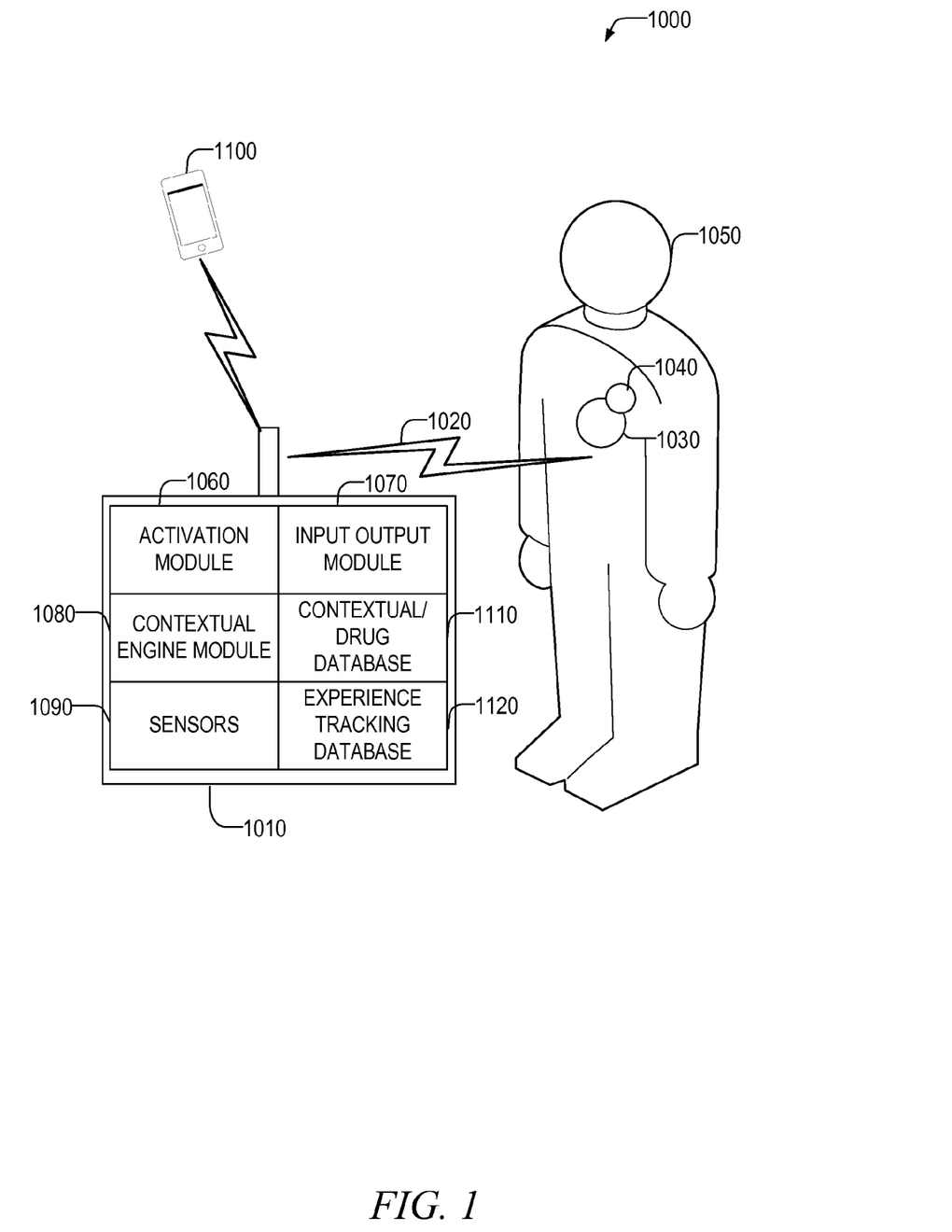
FIG. 1 shows a schematic of a system for contextual delivery of pharmaceuticals according to some examples of the present disclosure.

FIG. 1 shows a schematic 1000 of a system for contextual delivery of pharmaceuticals according to some examples of the present disclosure. Wearable device 1010 may emit an activation signal 1020 that causes pharmaceutical delivery agent 1030 to become activated, and in some examples release pharmaceutical 1040 in person 1050. Activation signal 1020 in some examples may include any signal that may cause pharmaceutical delivery agent 1030 to deliver a pharmaceutical. Example activation signals include a radio frequency signal, a magnetic field, an electrical field, a sound wave, and the like. The pharmaceutical delivery agent 1030 may be any container or molecule which may selectively release a pharmaceutical. Examples of pharmaceutical delivery agents 1030 may include nanoparticles, such as lipid-polymer nanoparticles.

A wearable device 1010 may include any device capable of being carried on or worn by a user and capable of contextual activation of a pharmaceutical in a person's body. Example devices that may be modified to include the functionality of the present disclosure may include prosthetics, orthotics, insulin pumps, and other ambulatory medical devices. Other example devices that may be modified to include the functionality of the present disclosure include smartphones, cellphones, tablets, laptops, and other computing devices. In some examples, to generate the required activation signal, devices may include an activation module 1060 that may be external to the device and communicatively linked to the device.

Wearable device 1010 may include an activation module 1060 that generates activation signal 1020 when commanded to by the contextual engine module 1080. Input and output module 1070 may receive configuration input from the user 1050, a pharmacist, doctor, or other authorized person that may configure the wearable device 1010. The input may be direct—e.g., through a provided user interface in the wearable device. The input may also be indirect—e.g., through a communications link with another computing device. The configuration may include the contexts under which the contextual engine module 1080 triggers the activation module 1060 to generate activation signal 1020.

Sensors 1090 may provide sensory input into the contextual engine module 1080. Sensors 1090 may be included in wearable device 1010. Other sensors not included in the wearable device may communicate with the wearable device 1010 through input and output module 1070 and provide input to contextual engine module 1080. For example, external device 1100 may have information on the user's schedule, activities, and other contextual inputs. External device 1100 may have one or more additional sensors to provide input into contextual engine module 1080.

Figure 2:
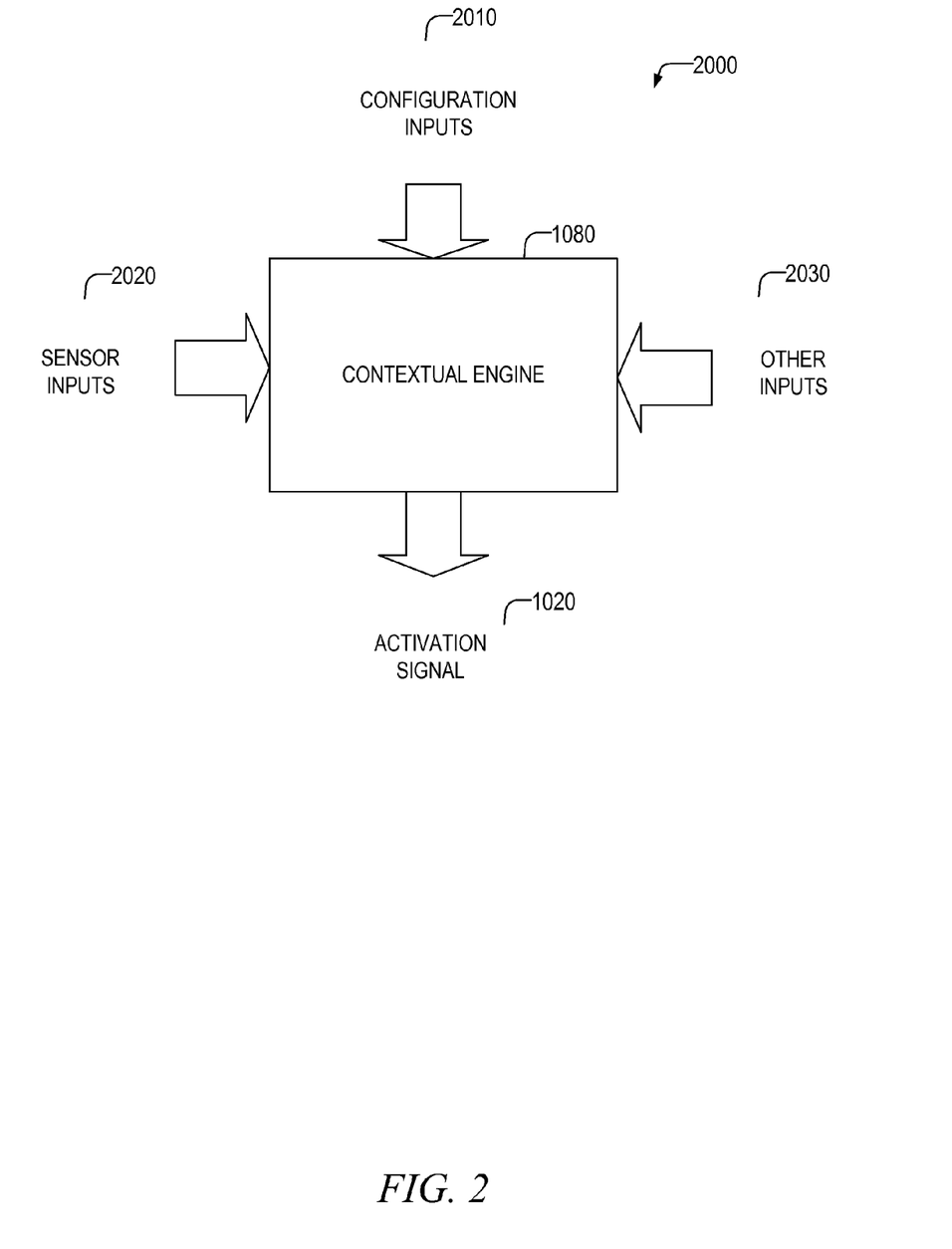
FIG. 2 shows a diagram of example inputs and outputs of contextual engine according to some examples of the present disclosure.

Contextual engine module 1080 may determine when to command activation module 1060 to send activation signal 1020 based upon sensor and other inputs. FIG. 2 shows a diagram 2000 of example inputs and outputs of contextual engine module 1080 according to some examples of the present disclosure. Contextual engine module 1080 may have configuration inputs 2010, sensor inputs 2020, and other inputs 2030 used to determine whether to output an activation signal 1020.

Example sensor inputs 2020 may include inputs from sensors that give the contextual engine an indication of the user's current activity level. Example sensors include an accelerometer, impact sensors, geolocation sensor, heart monitors and pulse monitors. For example, if the wearable device 1010 is a knee brace, the sensors may detect the start of physical activity by detecting movement of the knee brace. Once the start of physical activity has been detected, the wearable device 1010 may begin to activate a pharmaceutical such as an anti-inflammatory, or pain-relief drug. Other inputs may include input from sensors that give the contextual engine an indication of user biometrics, such as current bodily function. Examples include blood sugar monitors, blood oxygen sensors, brain wave sensors, heart monitors, and the like.

Other inputs 2030 may include the user's calendar, email contents, date and time information, point of interest information to provide information on a user's location, and the like. For example, certain locations may require the administration of a pharmaceutical. Examples include stressful places (e.g., a dentist's office), conversations with individuals that make the user stressed, locations where physical activity is expected to be exerted (e.g., a gym), and the like. Email analysis may be used to determine a user's future activities as well as a current job and personal stressful situations. Email analysis may include text analysis and Latent Dirichlet Analysis.

The contextual engine module 1080 may determine when to send activation signal 1020 in a number of ways. For example, contextual engine module 1080 may utilize a series of conditional statements such as "if-then" statements that use the values of the sensor inputs 2020 and the other inputs 2030. For example, if <a particular sensor reports a certain predetermined value> then send activation signal 1020. These if-then statements may be configured by a doctor, pharmacist, or other qualified individual and may be specified as part of configuration inputs 2010. Contextual engine module 1080 may include more complicated, nested, if-then statements that utilize one or more configuration inputs 2010, sensor inputs 2020, or other inputs 2030 in combination.

In other examples, contextual engine module 1080 may utilize machine learning techniques such as artificial neural networks. In these examples, the machine learning techniques may utilize training data to build a predictive model. The predictive model may then make predictions on whether newly received sensor inputs 2020, other inputs 2030, configuration inputs 2010, or the like indicate that a user's context is indicative of pharmaceutical activation.

In these examples, the training data may consist of past sensor inputs 2020 and other inputs 2030 along with an indication signal. The indication signal specifies whether or not the pharmaceutical should have been delivered based upon the past inputs. This indication signal may be provided directly by the user and may coincide with a manual activation of the pharmaceutical until the model is built. The indication signal may also be based on the outputs of certain sensors, such as biometric sensors. For example, if the pharmaceutical is insulin, the sensor inputs may include time of day, activity level, the user's schedule, and the like. The indication signal may be the user's glucose level. In this way the contextual engine module 1080 may learn which events trigger glucose levels that require activation of the pharmaceutical. In other examples, the doctor may determine when the pharmaceutical should have been administered to ensure the model is trained according to the doctor's judgment.

Other sensor inputs may also be utilized to train the contextual engine. For example, the contextual engine module 1080 may utilize the biometric sensors along with other contextual data to learn when the user is biologically stressed in a way which requires activation of a pharmaceutical. For example, the system may learn that when the user has a calendar appointment with a dentist, that they become emotionally stressed. The system may observe the appointment through the other inputs 2030 or through point of interest information which is matched to GPS inputs and observe an increased heartbeat, blood pressure, or other biometric indicating physical stress. If the user has a dentist appointment in the future, the contextual engine module 1080 may activate a relaxation pharmaceutical prior to the appointment such that the user is already relaxed upon arriving.

In any case, certain safeguards and controls that limit the amount of pharmaceutical activated may be used. For example, the system may be programmed to avoid activating more than a predetermined threshold limit of pharmaceutical in a predetermined time period. These limits may override the output of the if-then statements or the neural network.

Turning back to FIG. 1, the contextual/drug database 1110 may store information about safe dosages, parameters for determining contexts that trigger activation of the pharmaceutical, required dosages, how far in advance to administer a particular dosage, and in some examples, information used to train the contextual engine. Experience tracking database 1120 may store the user's past sensor data and past pharmaceutical activation history. This information may be used to generate a report to a doctor or other health care professional. This report may contain the sensor data and details about the pharmaceutical activation (e.g., time, date, quantity, and the like). In some examples, this past history data may be used as feedback to refine the model built by the machine learning algorithms. For example the experience tracking database 1120 may determine whether or not the pharmaceutical had the desired effect using sensor data before and after activation.

The components of FIG. 1 are shown as a single wearable unit 1010, but in other examples one or more of the modules 1060-1090 and 1110-1120 may be a standalone device, or part of a different device and communicate with the other components through one or more communication links.

Figure 3:
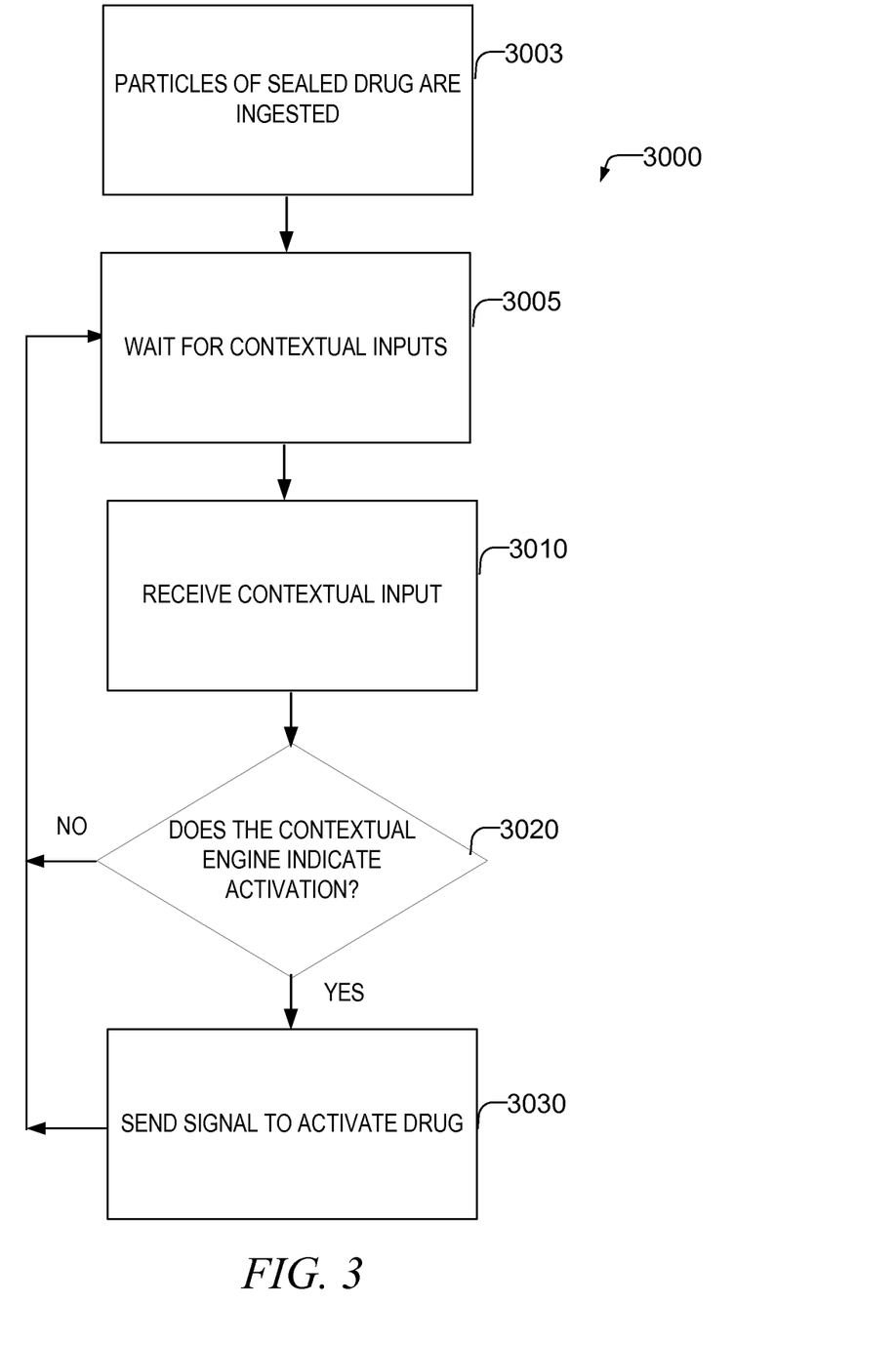
FIG. 3 shows a flowchart of a method of contextual activation of a pharmaceutical according to some examples of the present disclosure.

FIG. 3 shows a flowchart of a method 3000 of contextual activation of a pharmaceutical according to some examples of the present disclosure. In some examples at operation 3003 the user ingests the pharmaceutical sealed in a pharmaceutical delivery agent. At operation 3005, the wearable device waits for contextual inputs. At this point, the wearable device may not be sending a signal to activate the pharmaceutical. At operation 3010 a contextual input may be received. A contextual input may be any input which provides an indication of a context for the user. Inputs from sensors may indicate the user's current physical activities, current location, current stress and biometric levels, and the like. Input from other sources, such as a user's calendar or email contents may also indicate a user's current or predicted context.

At operation 3020, a determination is made as to whether the contextual inputs signal a context of the user that indicates the need for an activation of a pharmaceutical. The contextual engine may utilize one or more present or past contextual inputs (e.g., input 3010) and also any past inputs and past activations (e.g., to avoid overdoses) in making the determination. As already noted the contextual engine may be configured by an authorized user and may utilize if-then statements, decision trees, and other machine-learning algorithms such as a neural network, and the like. At operation 3030, if the contextual engine determines that activation is appropriate, the signal is sent to activate the pharmaceutical, which has been ingested by the patient in operation 3003. If the contextual engine does not indicate activation, or after the signal to activate has been sent at operation 3030, the wearable goes back to waiting for additional contextual inputs 3005.

In some examples, the signal to activate the drug 3030 may be of a specified duration, which is anticipated to activate a certain dosage of the pharmaceutical. In some examples, the contextual engine 3020 may vary the length and intensity of the activation signal in order to control the dosage. For example, the dosage of an anti-anxiety medication may be controlled such that small doses are administered in anticipation of events which are mildly stressful, whereas the signal may be sent longer and/or at a higher power level to administer larger doses in anticipation or response to events which are highly stressful. Additionally, the signal may be activated and deactivated over a particular time period. Thus, the signal activation may not be a single event, but rather a series of events over time.

In some cases, the activation of certain pharmaceuticals may be undesirable at certain times. For example, a drug that relaxes an individual may not be appropriate while they are operating an automobile. In some examples, the wearable device may require a user confirmation prior to activation of the pharmaceutical. In other examples, the user may be warned if they are engaging in an activity that is inconsistent or not recommended for a particular pharmaceutical. In other examples, the activation of the drug may be delayed until the user is no longer engaging in the activity. For example, activation of a sleep aid may be delayed because the user is driving but may be activated when the user arrives home.

Figure 4:
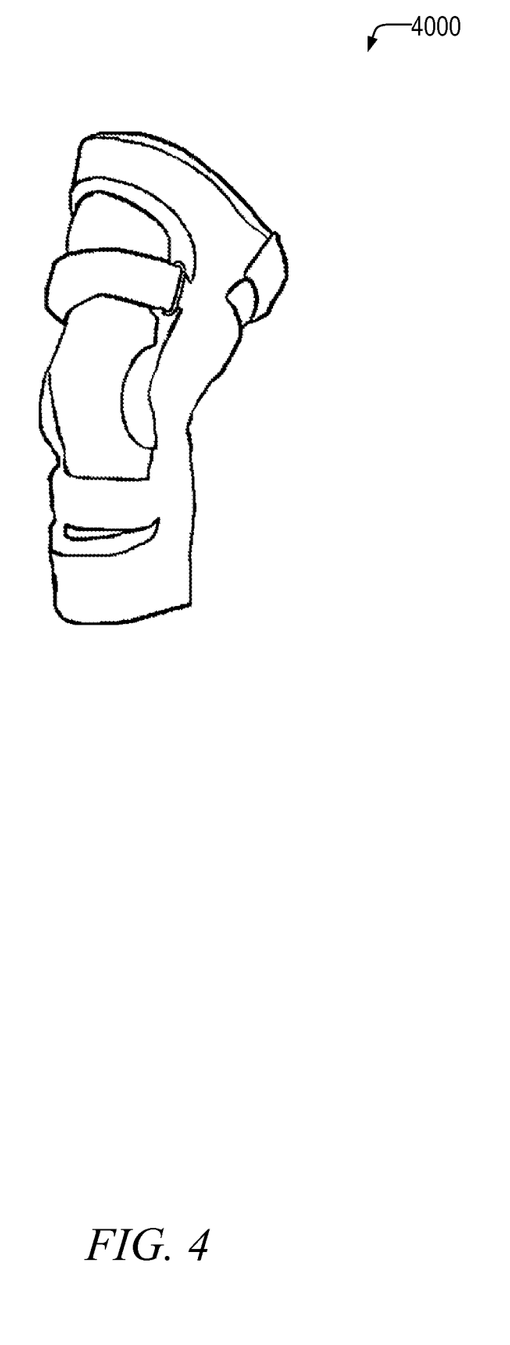
FIG. 4 illustrates a knee brace according to some examples of the present disclosure.

Additionally, the wearable device may be specific to a certain part of the user's body and the activation signal may be specific to that area. For example a wearable device in the form of a knee brace may activate a pain medication if activity is detected which may require pain medication at the site where the pain medication is needed—e.g., the knee. FIG. 4 illustrates a knee brace 4000 according to some examples of the present disclosure. In some examples, the knee brace may contain an integrated RF radio to activate a pharmaceutical in the knee in response to detecting a context that indicates activation is desired.

Figure 5:
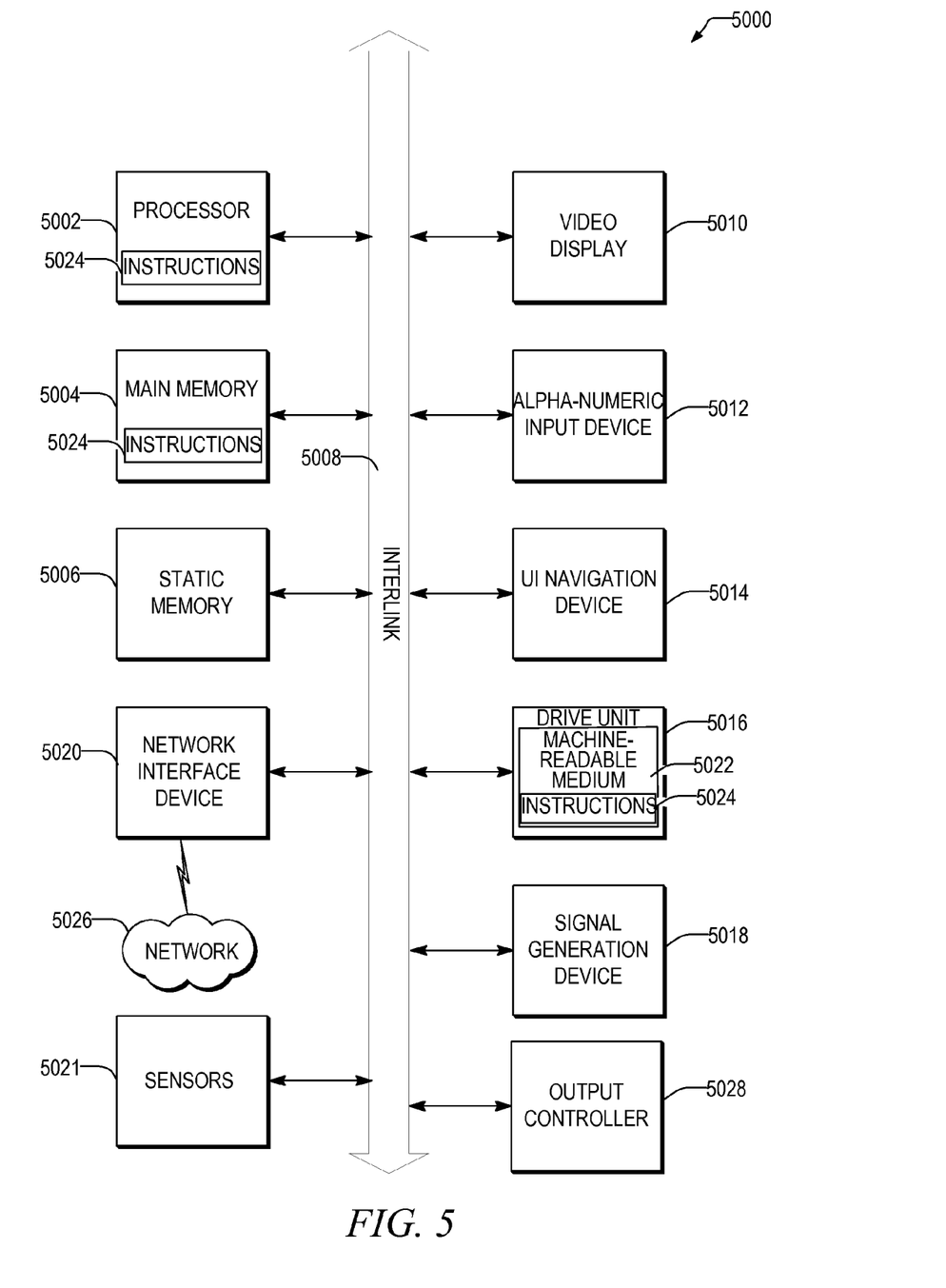
FIG. 5 is a schematic illustrating an example of a machine upon which one or more embodiments may be implemented.

FIG. 5 illustrates a schematic of an example machine 5000 upon which any one or more of the techniques (e.g., methodologies) discussed herein may perform. In alternative embodiments, the machine 5000 may operate as a standalone device or may be connected (e.g., networked) to other machines. In a networked deployment, the machine 5000 may operate in the capacity of a server machine, a client machine, or both in server-client network environments. In an example, the machine 5000 may act as a peer machine in peer-to-peer (P2P) (or other distributed) network environment. The machine 5000 may be a wearable device, personal computer (PC), a tablet PC, a set-top box (STB), a personal digital assistant (PDA), a mobile telephone, a smart phone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Machine (e.g., computer system) 5000 may include a hardware processor 5002 (e.g., a central processing unit (CPU), a graphics processing unit (GPU), a hardware processor core, or any combination thereof), a main memory 5004 and a static memory 5006, some or all of which may communicate with each other via an interlink (e.g., bus) 5008. The machine 5000 may further include a display unit 5010, an alphanumeric input device 5012 (e.g., a keyboard), and a user interface (UI) navigation device 5014 (e.g., a mouse). In an example, the display unit 5010, input device 5012 and UI navigation device 5014 may be a touch screen display. The machine 5000 may additionally include a storage device (e.g., drive unit) 5016, a signal generation device 5018 (e.g., a speaker), a network interface device 5020, and one or more sensors 5021, such as a global positioning system (GPS) sensor, compass, accelerometer, biometric, or other sensor. The machine 5000 may include an output controller 5028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 5016 may include a machine readable medium 5022 on which is stored one or more sets of data structures or instructions 5024 (e.g., software) embodying or utilized by any one or more of the techniques or functions described herein. The instructions 5024 may also reside, completely or at least partially, within the main memory 5004, within static memory 5006, or within the hardware processor 5002 during execution thereof by the machine 5000. In an example, one or any combination of the hardware processor 5002, the main memory 5004, the static memory 5006, or the storage device 5016 may constitute machine readable media.

While the machine readable medium 5022 is illustrated as a single medium, the term "machine readable medium" may include a single medium or multiple media (e.g., a centralized or distributed database, and/or associated caches and servers) configured to store the one or more instructions 5024.

The term "machine readable medium" may include any medium that is capable of storing, encoding, or carrying instructions for execution by the machine 5000 and that cause the machine 5000 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); Solid State Drives (SSD); and CD-ROM and DVD-ROM disks. In some examples, machine readable media may include non-transitory machine readable media. In some examples, machine readable media may include machine readable media that is not a transitory propagating signal.

The instructions 5024 may further be transmitted or received over a communications network 5026 using a transmission medium via the network interface device 5020. The machine 5000 may communicate with one or more other machines utilizing any one of a number of transfer protocols (e.g., frame relay, Internet Protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others. In an example, the network interface device 5020 may include one or more physical jacks (e.g., Ethernet, coaxial, or phone jacks) or one or more antennas to connect to the communications network 5026. In an example, the network interface device 5020 may include a plurality of antennas to wirelessly communicate using at least one of single-input multiple-output (SIMO), multiple-input multiple-output (MIMO), or multiple-input single-output (MISO) techniques. In some examples, the network interface device 5020 may wirelessly communicate using Multiple User MIMO techniques.

Other Notes and Examples

Example 1 includes subject matter (such as a method, means for performing acts, machine readable storage medium including instructions that, when performed by a machine cause the machine to performs acts, or an apparatus configured to perform) for contextual activation of a pharmaceutical comprising: using one or more processors: receiving a contextual input, the contextual input indicative of a context of a user; determining, based upon the contextual input, that activation of a pharmaceutical in the user is indicated; and responsive to determining that activation of the pharmaceutical in the user is indicated, sending a signal to activate the pharmaceutical.

In example 2, the subject matter of example 1 may include wherein the context of the user is a future situation in which the pharmaceutical activation in a user is indicated.

In example 3, the subject matter of any one or more of examples 1-2 may include wherein sending the signal to activate the pharmaceutical is timed by the one or more processors such that the pharmaceutical is activated when the future situation is predicted by the one or more processors to occur.

In example 4, the subject matter of any one or more of examples 1-3 may include wherein the contextual input includes one of: an output from a biometric sensor, a calendar event, a position of the wearable device, an acceleration of the wearable device, or an inferred user activity based on analysis of sensor data.

In example 5, the subject matter of any one or more of examples 1-4 may include wherein determining that activation of the pharmaceutical is indicated is based upon the contextual input and a configuration input.

In example 6, the subject matter of any one or more of examples 1-5 may include wherein the configuration input is a conditional statement and the contextual input is a variable within the conditional statement.

In example 7, the subject matter of any one or more of examples 1-6 may include wherein determining that activation of the pharmaceutical is indicated comprises using a neural network to make the determination, wherein the contextual input is an input into the neural network.

In example 8, the subject matter of any one or more of examples 1-7 may include training the neural network based upon a past contextual input and a corresponding indication signal from a biometric sensor.

In example 9, the subject matter of any one or more of examples 1-8 may include training the neural network based upon a past contextual input and an indication of whether the pharmaceutical should have been activated or not.

In example 10, the subject matter of any one or more of examples 1-9 may include wherein determining that activation of the pharmaceutical is indicated comprises using a decision tree to make the determination, wherein the contextual input is an input into the decision tree.

In example 11, the subject matter of any one or more of examples 1-10 may include wherein the signal to activate the pharmaceutical comprises a magnetic field.

In example 12, the subject matter of any one or more of examples 1-11 may include wherein the signal to activate the pharmaceutical comprises a radio frequency signal.

In example 13, the subject matter of any one or more of examples 1-12 may include controlling the dosage by adjusting a duration of the signal.

In example 14, the subject matter of any one or more of examples 1-13 may include controlling the dosage by adjusting an intensity of the signal.

In example 15, the subject matter of any one or more of examples 1-14 may include wherein one or more processors is included in a wearable device.

In example 16, the subject matter of any one or more of examples 1-15 may include receiving a second contextual input after the signal to activate the pharmaceutical has been sent; and responsive to receiving the second contextual input generating a report containing the contextual input and the second contextual input.

Example 17, includes (or may optionally be combined with the subject matter of any one of Examples 1-16 to include) subject matter (such as a device, apparatus, or machine) comprising A device for contextual activation of a pharmaceutical comprising: an activation module configured to send a signal to activate a pharmaceutical; a contextual engine module configured to: receive a contextual input, the contextual input indicative of a context of a user; determine, based upon the contextual input, that activation of a pharmaceutical in the user is indicated; and cause the activation module to send the signal to activate the pharmaceutical responsive to determining that activation of the pharmaceutical in the user is indicated.

In example 18, the subject matter of any one or more of examples 1-17 may include wherein the context of the user is a future situation in which the pharmaceutical activation in a user is indicated.

In example 19, the subject matter of any one or more of examples 1-18 may include wherein the contextual engine module is configured to send the signal to activate the pharmaceutical by timing the sending of the signal such that the pharmaceutical is activated when the future situation is predicted by the contextual engine module to occur.

In example 20, the subject matter of any one or more of examples 1-19 may include wherein the contextual input includes one of: an output from a biometric sensor, a calendar event, a position of the wearable device, an acceleration of the wearable device, or an inferred user activity based on analysis of sensor data.

In example 21, the subject matter of any one or more of examples 1-20 may include wherein the contextual engine module is configured to determine that activation of the pharmaceutical is indicated based upon the contextual input and a configuration input.

In example 22, the subject matter of any one or more of examples 1-21 may include wherein the configuration input is a conditional statement and the contextual input is a variable within the conditional statement.

In example 23, the subject matter of any one or more of examples 1-22 may include wherein the contextual engine module is configured to determine that activation of the pharmaceutical is indicated based upon output of a neural network, wherein the contextual input is an input into the neural network.

In example 24, the subject matter of any one or more of examples 1-23 may include wherein the contextual engine module is configured to train the neural network based upon a past contextual input and a corresponding indication signal from a biometric sensor.

In example 25, the subject matter of any one or more of examples 1-24 may include wherein the contextual engine module is configured to train the neural network based upon a past contextual input and an indication of whether the pharmaceutical should have been activated or not.

In example 26, the subject matter of any one or more of examples 1-25 may include wherein the contextual engine module is configured to determine that activation of the pharmaceutical is indicated based upon an output of a decision tree, wherein the contextual input is an input into the decision tree.

In example 27, the subject matter of any one or more of examples 1-26 may include wherein the signal to activate the pharmaceutical comprises a magnetic field.

In example 28, the subject matter of any one or more of examples 1-27 may include wherein the signal to activate the pharmaceutical comprises a radio frequency signal.

In example 29, the subject matter of any one or more of examples 1-28 may include wherein the contextual engine module is configured to control the dosage by adjusting a duration of the signal.

In example 30, the subject matter of any one or more of examples 1-29 may include wherein the contextual engine module is configured to control the dosage by adjusting an intensity of the signal.

In example 31, the subject matter of any one or more of examples 1-30 may include wherein the device is integrated into an orthotic.

In example 32, the subject matter of any one or more of examples 1-31 may include wherein the contextual engine module is configured to: receive a second contextual input after the signal to activate the pharmaceutical has been sent; and generate a report containing the contextual input and the second contextual input responsive to receiving the second contextual input.

Example 33 includes (or may optionally be combined with the subject matter of any one of Examples 1-32 to include) subject matter (such as a means for performing acts) for contextual activation of a pharmaceutical comprising: means for receiving a contextual input, the contextual input indicative of a context of a user; means for determining, based upon the contextual input, that activation of a pharmaceutical in the user is indicated; and means for sending a signal to activate the pharmaceutical responsive to determining that activation of the pharmaceutical in the user is indicated.

In example 34, the subject matter of any one or more of examples 1-33 may include wherein the context of the user is a future situation in which the pharmaceutical activation in a user is indicated.

In example 35, the subject matter of any one or more of examples 1-34 may include wherein sending the signal to activate the pharmaceutical is timed by the means for determining such that the pharmaceutical is activated when the future situation is predicted by the means for determining.

In example 36, the subject matter of any one or more of examples 1-35 may include wherein the contextual input includes one of: an output from a biometric sensor, a calendar event, a position of the wearable device, an acceleration of the wearable device, or an inferred user activity based on analysis of sensor data.

In example 37, the subject matter of any one or more of examples 1-36 may include wherein determining that activation of the pharmaceutical is indicated is based upon the contextual input and a configuration input.

In example 38, the subject matter of any one or more of examples 1-37 may include wherein the configuration input is a conditional statement and the contextual input is a variable within the conditional statement.

In example 39, the subject matter of any one or more of examples 1-38 may include wherein determining that activation of the pharmaceutical is indicated comprises using a neural network to make the determination, wherein the contextual input is an input into the neural network.

In example 40, the subject matter of any one or more of examples 1-39 may include means for training the neural network based upon a past contextual input and a corresponding indication signal from a biometric sensor.

In example 41, the subject matter of any one or more of examples 1-40 may include means for training the neural network based upon a past contextual input and an indication of whether the pharmaceutical should have been activated or not.

In example 42, the subject matter of any one or more of examples 1-41 may include wherein the means for determining that activation of the pharmaceutical is indicated comprises using a decision tree to make the determination, wherein the contextual input is an input into the decision tree.

In example 43, the subject matter of any one or more of examples 1-42 may include wherein the signal to activate the pharmaceutical comprises a magnetic field.

In example 44, the subject matter of any one or more of examples 1-43 may include wherein the signal to activate the pharmaceutical comprises a radio frequency signal.

In example 45, the subject matter of any one or more of examples 1-44 may include means for controlling the dosage by adjusting a duration of the signal.

In example 46, the subject matter of any one or more of examples 1-45 may include means for controlling the dosage by adjusting an intensity of the signal.

In example 47, the subject matter of any one or more of examples 1-46 may include wherein one or more processors is included in a wearable device.

In example 48, the subject matter of any one or more of examples 1-47 may include means for receiving a second contextual input after the signal to activate the pharmaceutical has been sent; and means for generating a report containing the contextual input and the second contextual input responsive to receiving the second contextual input.

Example 49 includes (or may optionally be combined with the subject matter of any one of Examples 1-48 to include) subject matter (such as a machine-readable storage medium) for contextual activation of a pharmaceutical comprising: comprising: receiving a contextual input, the contextual input indicative of a context of a user; determining, based upon the contextual input, that activation of a pharmaceutical in the user is indicated; and responsive to determining that activation of the pharmaceutical in the user is indicated, sending a signal to activate the pharmaceutical.

In example 50, the subject matter of any one or more of examples 1-49 may include wherein the context of the user is a future situation in which the pharmaceutical activation in a user is indicated.

In example 51, the subject matter of any one or more of examples 1-50 may include wherein the operations for sending the signal to activate the pharmaceutical comprise operations to time the signal such that the pharmaceutical is activated when the future situation is predicted to occur.

In example 52, the subject matter of any one or more of examples 1-51 may include wherein the contextual input includes one of: an output from a biometric sensor, a calendar event, a position of the wearable device, an acceleration of the wearable device, or an inferred user activity based on analysis of sensor data.

In example 53, the subject matter of any one or more of examples 1-50 may include wherein the operations for determining that activation of the pharmaceutical is indicated includes operations for determining that activation of the pharmaceutical is indicated based upon the contextual input and a configuration input.

In example 54, the subject matter of any one or more of examples 1-53 may include wherein the configuration input is a conditional statement and the contextual input is a variable within the conditional statement.

In example 55, the subject matter of any one or more of examples 1-54 may include wherein the operations for determining that activation of the pharmaceutical is indicated includes using a neural network to make the determination, wherein the contextual input is an input into the neural network.

In example 56, the subject matter of any one or more of examples 1-55 may include wherein the operations comprise training the neural network based upon a past contextual input and a corresponding indication signal from a biometric sensor.

In example 57, the subject matter of any one or more of examples 1-56 may include wherein the operations comprise training the neural network based upon a past contextual input and an indication of whether the pharmaceutical should have been activated or not.

In example 58, the subject matter of any one or more of examples 1-57 may include wherein the operations for determining that activation of the pharmaceutical is indicated includes using a decision tree to make the determination, wherein the contextual input is an input into the decision tree.

In example 59, the subject matter of any one or more of examples 1-58 may include wherein the signal to activate the pharmaceutical comprises a magnetic field.

In example 60, the subject matter of any one or more of examples 1-59 may wherein the signal to activate the pharmaceutical comprises a radio frequency signal.

In example 61, the subject matter of any one or more of examples 1-60 may wherein the operations comprise controlling the dosage by adjusting a duration of the signal.

In example 62, the subject matter of any one or more of examples 1-61 may wherein the operations comprise controlling the dosage by adjusting an intensity of the signal.

In example 63, the subject matter of any one or more of examples 1-62 may wherein the operations comprise: receiving a second contextual input after the signal to activate the pharmaceutical has been sent; and responsive to receiving the second contextual input generating a report containing the contextual input and the second contextual input.

What is claimed is:
1. A device for contextual activation of a pharmaceutical comprising:
a hardware processor configured to include:
an activation module configured to send an electronic signal to activate a pharmaceutical; and
a contextual engine module to:
receive a contextual input, the contextual input indicative of a context of a user, the context of the user being a current location of the user or a future predicted location of the user;
determine, based upon the contextual input, that activation of a pharmaceutical in a user is indicated, the pharmaceutical already circulating in the blood stream of the user prior to the receipt of the contextual input; and
cause the activation module to send the electronic signal to activate the pharmaceutical to provide a therapy responsive to determining that activation of the pharmaceutical in the user is indicated.

2. The device of claim 1, wherein the contextual engine module is to determine that activation of the pharmaceutical is indicated is based upon an output of a decision tree, wherein the contextual input is an input into the decision tree.

3. The device of claim 1, wherein the contextual engine module is to control a dosage released by adjusting a duration of the electronic signal.

4. The device of claim 1 wherein the contextual engine module is to control a dosage released by adjusting an intensity of the electronic signal.

5. The device of claim 1, wherein the device is integrated into an orthotic.

6. The device of claim 1, wherein the contextual engine module is to:
receive a second contextual input after the electronic signal to activate the pharmaceutical has been sent; and
generate a report containing the contextual input and the second contextual input responsive to receiving the second contextual input.

7. A non-transitory machine-readable storage medium that stores instructions which when performed by a machine, cause the machine to perform operations to:
receive a contextual input, the contextual input indicative of a context of a user, the context of the user being a current location of the user or a future predicted location of the user;
determine, based upon the contextual input, that activation of a pharmaceutical in the user is indicated, the pharmaceutical already circulating in the blood stream of the user prior to the receipt of the contextual input; and
responsive to determining that activation of the pharmaceutical in the user is indicated, send an electronic activation signal to activate the pharmaceutical to provide a therapy.

8. The machine-readable medium of claim 7, wherein the context of the user is a predicted future situation in which the pharmaceutical activation in a user is indicated.

9. The machine-readable medium of claim 8, wherein the operations to send the electronic activation signal to activate the pharmaceutical comprise operations to time the electronic activation signal such that the pharmaceutical is activated when the predicted future situation is predicted to occur.

10. The machine-readable medium of claim 7, wherein the contextual input includes one of:
an output from a biometric sensor, a calendar event, a position of a wearable device, an acceleration of the wearable device, or an inferred user activity based on analysis of sensor data.

11. The machine-readable medium of claim 7, wherein the operations to determine that activation of the pharmaceutical is indicated includes operations to determine that activation of the pharmaceutical is indicated based upon the contextual input and a configuration input.

12. The machine-readable medium of claim 11, wherein the configuration input is a conditional statement and the contextual input is a variable within the conditional statement.

13. The machine-readable medium of claim 7, wherein the operations to determine that activation of the pharmaceutical is indicated includes using a neural network to make the determination, wherein the contextual input is an input into the neural network.

14. The machine-readable medium of claim 13, wherein the instructions comprise instructions to cause the machine to train the neural network based upon a past contextual input and a corresponding indication signal from a biometric sensor.

15. The machine-readable medium of claim 13, wherein the instructions comprise instructions to cause the machine to train the neural network based upon a past contextual input and an indication of whether the pharmaceutical should have been activated or not.

16. The machine-readable medium of claim 7, wherein the operations for determining that activation of the pharmaceutical is indicated includes using a decision tree to make the determination, wherein the contextual input is an input into the decision tree.

17. The machine-readable medium of claim 7 wherein the instructions comprise instructions to cause the machine to control a dosage by adjusting a duration of the electronic activation signal.

18. The machine-readable medium of claim 7 wherein the instructions comprise instructions to cause the machine to control a dosage by adjusting an intensity of the electronic activation signal.

19. A method for contextual activation of a pharmaceutical comprising:
    using one or more processors:
        receiving a contextual input, the contextual input indicative of a context of a user, the context of the user being a current location of the user or a future predicted location of the user
        determining, based upon the contextual input, that activation of a pharmaceutical in a user is indicated, the pharmaceutical already circulating in the blood stream of the user prior to receipt of the contextual input; and
        responsive to determining that activation of the pharmaceutical in the user is indicated, sending an electronic signal to activate the pharmaceutical to provide a therapy.

20. The method of claim 19, wherein the context of the user is a predicted future situation in which the pharmaceutical activation in a user is indicated.

21. The method of claim 19, wherein the contextual input includes one of:
    an output from a biometric sensor, a calendar event, a position of a wearable device, an acceleration of the wearable device, or an inferred user activity based on analysis of sensor data.

22. The method of claim 19, wherein determining that activation of the pharmaceutical is indicated is based upon the contextual input and a configuration input.

23. The method of claim 22, wherein the configuration input is a conditional statement and the contextual input is a variable within the conditional statement.

24. The method of claim 19, wherein determining that activation of the pharmaceutical is indicated comprises using a neural network to make the determination, wherein the contextual input is an input into the neural network.

25. The method of claim 19, wherein determining that activation of the pharmaceutical is indicated comprises using a decision tree to make the determination, wherein the contextual input is an input into the decision tree.

* * * * *

UNITED STATES PATENT AND TRADEMARK OFFICE
CERTIFICATE OF CORRECTION

PATENT NO. : 10,004,883 B2
APPLICATION NO. : 14/497051
DATED : June 26, 2018
INVENTOR(S) : Glen J. Anderson It is certified that error appears in the above-identified patent and that said Letters Patent is hereby corrected as shown below:

In the Claims

In Column 16, Line 4, in Claim 19, after "user", insert --;--

Signed and Sealed this
Fourth Day of June, 2019

Andrei Iancu
*Director of the United States Patent and Trademark Office*